United States Patent
Jensen et al.

(12)

(10) Patent No.: US 6,592,888 B1
(45) Date of Patent: Jul. 15, 2003

(54) COMPOSITION FOR WOUND DRESSINGS SAFELY USING METALLIC COMPOUNDS TO PRODUCE ANTI-MICROBIAL PROPERTIES

(75) Inventors: Jarl B. Jensen, River Vale, NJ (US); Anil Torjalkar, Cranbury, NJ (US)

(73) Assignee: Jentec, Inc., Northvale, NJ (US)

( * ) Notice: Subject to any disclaimer, the term of this patent is extended or adjusted under 35 U.S.C. 154(b) by 0 days.

(21) Appl. No.: 09/584,558

(22) Filed: May 31, 2000

(51) Int. Cl.⁷ .......................... A61F 13/00; A61L 15/00; A61K 9/16
(52) U.S. Cl. .................. 424/443; 424/445; 424/446; 424/447; 424/448; 424/490
(58) Field of Search ................................ 424/400, 401, 424/411, 443

(56) References Cited

U.S. PATENT DOCUMENTS

| | | | |
|---|---|---|---|
| 4,525,410 A | * 6/1985 | Hagiwara et al. | 424/411 |
| 5,100,671 A | * 3/1992 | Maeda et al. | 424/443 |
| 5,151,122 A | * 9/1992 | Atsumi et al. | 106/18.36 |
| 6,143,798 A | * 11/2000 | Jensen et al. | 514/772.1 |
| 6,303,138 B1 | * 10/2001 | Peterson et al. | 424/400 |

* cited by examiner

Primary Examiner—Gollamudi S. Kishore
Assistant Examiner—Isis Ghali
(74) Attorney, Agent, or Firm—McDonnell Boehnen Hulbert & Berghoff

(57) ABSTRACT

A wound dressing having a metallic compound as an anti-microbial agent. The dressing includes a dressing layer that contacts a patient's skin at the wound bed. The composition of the dressing layer includes metallic compounds in which metallic ions, such as silver, are maintained in the dressing composition. The metallic compound is combined with a hydrocolloid adhesive to provide a highly absorbing dressing. As exudate is absorbed, contact with the metallic ions provides the anti-microbial effect. The metallic ions may be maintained in compounds such as zeolite and hydroxyl apatite mixed with a hydrocolloid adhesive.

6 Claims, 2 Drawing Sheets

FIG. IA
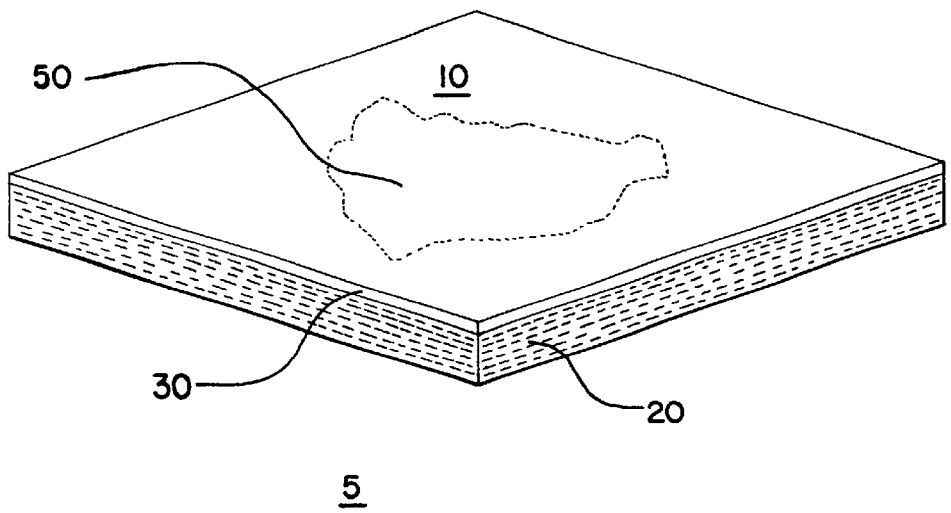
FIG. IB
DIRECTION OF FLOW OF WOUND EXUDATE
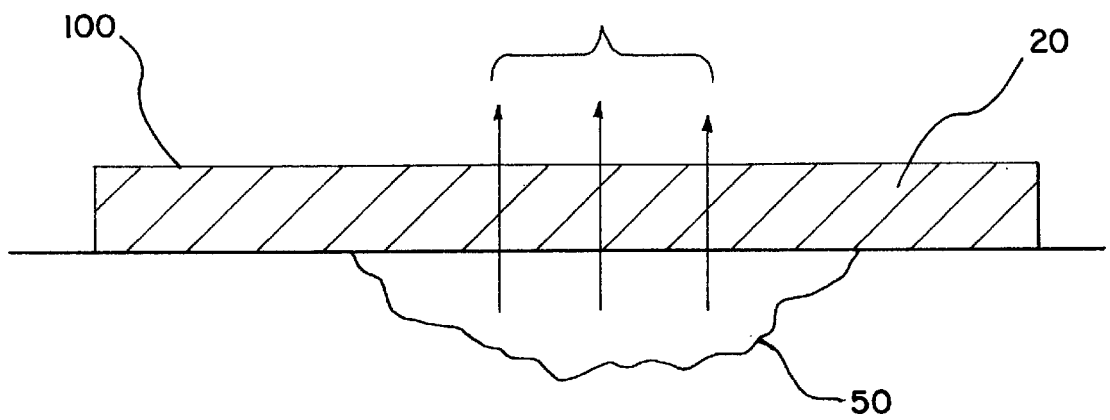

COMPOSITION FOR WOUND DRESSINGS SAFELY USING METALLIC COMPOUNDS TO PRODUCE ANTI-MICROBIAL PROPERTIES

FIELD OF THE INVENTION

The present invention relates to the field of dressings, and more particularly to the field of dressings for wounds, surgical cuts and other lesions to the human skin with anti-microbial properties.

DESCRIPTION OF RELATED ART

Silver and other metals have been long recognized as being effective disinfecting agents. Compounds having a metal component that cause a metal ion exchange in the presence of a solution have been shown to destroy and inhibit the growth of many types of microbes, such as bacteria, fungus and other organisms. Silver nitrate is one well-known compound that is used as a disinfectant, but only in limited circumstances because it is primarily available in solution form. Silver is also used in pharmaceutical compositions, such as silver sulphadiazine, in the form of an ointment for topical application. Such applications complicate the wound treatment process by requiring a step to apply the anti-microbial agent, and a step to add the dressing.

It would be desirable to provide wound-dressing devices with metal-based disinfecting agents to provide the devices with a disinfecting function without additional steps in the wound treatment. Some known dressings use silver and other metals as disinfecting agents either in their sold metal state, or in the form of soluble compounds, such as soluble salts of acetate or nitrate. When applied to an exudating wound, silver ions are released into the wound as the molecules are dissolved. Such solutions tend to be inefficient, however, since the silver ions may react with ions from the exudate leaving few free silver ions for disinfecting.

Another problem with using metals as disinfecting agents in the treatment of open wounds is that metals may be toxic in sufficiently large amounts. If a metal such as silver were to be applied to open wounds, it may enter the bloodstream and end up absorbed by the human body. Once present in the body, silver is not expelled by normal bodily functions and may become imbedded in vital organs such as the liver or the brain.

One dressing uses an inorganic material described in U.S. Pat. No. 5,470,585 to Gilchrist (hereinafter Gilchrist), which consists of a fused mass of sodium and calcium phosphates containing small amounts of silver phosphate. The material is attached to a film dressing and offered as a commercial product called Arglaes™ Controlled Release Island Dressings by Maersk Medical Inc.

The material of the Arglaes™ Controlled Release Dressing releases free silver ions in the presence of an aqueous solution. The material is designed to dissolve completely over a period of several days such that the amount of free silver at any one time is small. When in contact with the aqueous solution, the material dissolves at a rate dependent upon the relative proportions of the readily soluble sodium phosphates and less soluble calcium phosphates present with the release of sodium, calcium, phosphate and silver ions into the solution. The material is impregnated, or mounted on the wound-contacting surface of a polyurethane film. In one example, the material is impregnated in a calcium alginate pad, which is affixed to a polyethylene film.

One problem with the device disclosed in Gilchrist is that the dressing does not maintain the silver ions in the dressing. The silver ions are released into the wound at a rate dependent upon the sodium content and the amount of moisture at the wound site. In addition to potentially being toxic to the patient, the anti-microbial action is sub-optimal. Bacteria are killed at a rate that is dependent on the release of the silver into the wound site, which may not be fast enough. Arglaes™ Controlled Release Island Dressings are described as requiring 2 days to achieve a 99% reduction of bacteria.

It would be desirable to provide a wound dressing that employs silver or other metal ions as a disinfecting agent without releasing the ions into the wound site. It would also be desirable for such a wound dressing to effectively absorb moisture at a wound-site and to be conformable, flexible and easy to apply and remove.

Silver and other disinfecting metals have been used with various compositions as anti-microbial compositions, but few have been applied to a wound dressing.

U.S. Pat. No. 4,525,410 to Hagiwara et al. (hereinafter Hagiwara I) discloses a fiber article having anti-bacterial properties using zeolite particles that retain metal ions. The zeolite is treated with silver nitrate, mixed with various plastic materials, and heat-treated to obtain a fluffy, fibrous article. Hagiwara I does not describe precisely how the fibrous article may be applied, but mentions pillows, mats, beds, bedclothes and insoles of shoes as examples of articles that may apply the article. Hagiwara I does not disclose how or if the fibrous article may be used in medical devices.

Similarly, U.S. Pat. No. 4,775,585 to Hagiwara et al. (hereinafter Hagiwara II) describes polymer articles having antibacterial properties using zeolite. Hagiwara II discloses that such articles may be used as granules, films, fibers, pipes, or other molded articles but lacks any teaching as to the use of such articles in wound treatment.

U.S Pat. No. 5,556,699 to Niira discloses an antibiotic film having at least one organic polymeric film containing antibiotic zeolite. The film disclosed in Niira is less than 15 microns which permits it to maintain transparency. The film is used as a packaging material for packaging foods and medical equipment. No mention is made of its use in wound treatment.

In view of the above, a wound dressing and wound dressing materials are provided that use compositions that incorporate silver and other metals for anti-microbial action. The dressing and dressing materials of the present invention are advantageously highly-absorbent, and protect the wound-site with a high bacteria kill rate. The anti-microbial effect is accomplished using silver or other metal ions maintained in a composition that permits little or no leakage of the metal into the wound-site.

SUMMARY OF THE INVENTION

In one aspect of the present invention, a dressing for application on a skin opening is provided having a substantially planar dressing layer. The dressing layer has a skin-contacting surface, and hydrocolloid-adhesive composition mixed with an anti-microbial agent. The anti-microbial agent includes a metallic composition operable to provide disinfecting actions. The hydrocolloid-adhesive composition and anti-microbial agent mixture bind the metallic composition to prevent leakage of the metallic ions into the skin opening.

BRIEF DESCRIPTION OF THE DRAWINGS

Presently preferred embodiments of the invention are described below in conjunction with the appended drawing figures, wherein like reference numerals refer to like elements in the various figures, and wherein:

FIG. 1A is a perspective view of an area of skin having a dressing with anti-microbial properties in accordance with a preferred embodiment of the present invention;

FIG. 1B is a cross-sectional view of the area of skin shown in FIG. 1A;

DETAILED DESCRIPTION OF THE PREFERRED EMBODIMENT

A. Wound Dressing Having Anti-Microbial Affects

Figure 2:
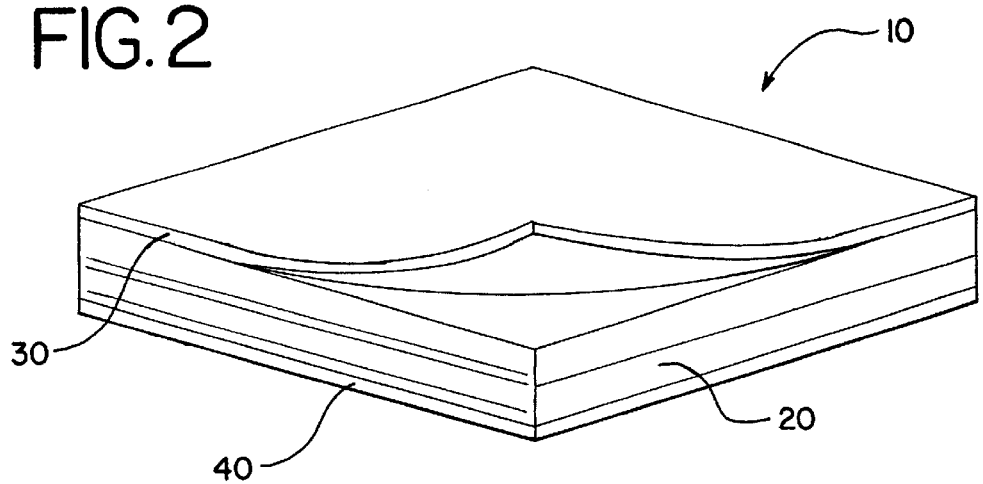
FIG. 2 is a perspective view of a product configuration of the dressing of FIG. 1.

FIG. 1A shows a dressing 10 according to an embodiment of the present invention applied over an area of skin 5 having a skin opening 50. The dressing 10 includes a dressing layer 20 and a backing layer 30. The shape of the dressing 10 in FIG. 1 is rectangular, however, the dressing 10 may have any shape, and may also include an inner hole for use as an ostomy wafer.

The dressing layer 20 is preferably a hydrocolloid-adhesive composition having an anti-microbial agent. The anti-microbial agent includes metallic compounds that provide anti-microbial effects by killing bacteria with contact with metallic ions. The hydrocolloid-adhesive composition and anti-microbial agent structurally bind or maintain the metallic particles from leaking metallic ions into the skin opening 50. The hydrocolloid-adhesive composition also exhibits highly absorptive capabilities that act to maintain the metallic compound within the adhesive dressing. By preventing leakage of the metallic composition into the skin opening 50, the dressing 10 achieves suitable anti-microbial effects without the toxic side effects typically associated with the release of metal ions into the wound bed.

FIG. 1B is a cross-sectional view of the area of skin 5 of FIG. 1A in which the dressing 10 is applied to the skin opening 50. The dressing layer 20 includes metallic compound particles 100 distributed throughout to provide the anti-microbial action of the dressing 10. Typically, the skin opening 50 at the wound site collects wound exudate, particularly when the wound is fresh. This exudate provides a suitable environment for the growth of bacteria and other microbes that may lead to serious infection if left untreated.

Dressings that use hydrocolloid adhesives such as those disclosed in U.S. Pat. No. 5,571,080 to Jensen (incorporated herein by reference) have water-swellable properties that allow the material to swell to many times its normal size. In addition, once the moisture is absorbed by the material, it is maintained within the dressing structure.

FIG. 1B shows the direction in which exudate is absorbed into the dressing layer 20 of the dressing 10 from the skin opening 50. Because the hydrocolloid adhesive material in the dressing layer maintains the moisture from the exudate, the skin opening 50 is left relatively moist, but without excessive exudate. In addition, the metallic compound 100 maintained in the dressing layer 20 destroy bacteria and other microbes thereby providing a disinfecting action to the wound healing environment. One advantage of the dressing layer 20 is that the metallic compound 100 is maintained within the dressing layer structure such that they do not leach out into the skin opening 50. The disinfecting action is therefore maintained optimal for the duration of time that the dressing 10 is maintained on the skin opening 50. In addition, any toxic effects that may be caused by the metallic compound 100 are eliminated.

The dressing 10 may be packaged in a variety of ways that are suitable to the intended application. In a preferred embodiment, a protective covering and a release sheet are attached to the dressing. Referring to FIG. 2, a release sheet 40 is provided on the wound-contacting surface of the dressing 10. The release sheet 40 is a protective covering that is to be removed during the application of the dressing. In a wound dressing, the release sheet 40 is preferably made of a silicone release paper or other flexible material treated for easy removal from the dressing layer 10. Other materials include polyester and polypropylene films.

The protective cover layer 30 may be provided as a protective covering for the dressing layer 10 on the side opposite the skin-contacting surface of the dressing 10. In the wound dressing 10, the protective cover layer 30 may be made of co-polyester, ethyl vinyl acetate, polyether block amide, polyethylene pulp non-woven, polyurethane film, polyethylene film, non-woven, or other suitable film may be used as a protective cover for the dressing layer 10. Other materials may be used for the protective cover layer 30 depending on the function of the dressing layer 10.

B. Compositions of Dressing layer

1. Composition With Zeolite

In a preferred embodiment, the ion exchange between metal ions and other ions produces the anti-microbial affects of the dressing 10. The metal ions are contained in the anti-microbial agent in a manner that maintains the ion exchange of the metal ions such that the metal ions do not react with other compounds. In one preferred embodiment, the metal ions are contained in the matrix structure of an inorganic polymer composed of zeolite particles. The matrix structure is advantageously micro-porous to permit contact between the microbes in the exudate with the metal ions contained in the matrix structure. Silver ions are preferred, however, copper, zinc and any other metal having anti-microbial affects may also be used.

Zeolite is, in general, an aluminosilicate having a three-dimensionally grown skeleton structure, which provides the matrix structure for containing the silver ions. Zeolites that may be used in the present invention are described in U.S. Pat. No. 4,775,585 to Hagiwara et al. (incorporated herein by reference). A preferred embodiment of the present invention uses the zeolite commercially known as Bactekilleri available from Kanebo Ltd. of Japan.

Alternatively, the silver or other metal ions may be maintained in a matrix structure of inorganic polymer comprising a calcium or zinc phosphate compound having stabilized $Ag^+$ admixed therein. The silver is permanently bonded to inorganic phosphate crystals to prevent leaching into the wound site. In one embodiment, the inorganic polymer used is hydroxy apatite.

Preferred inorganic polymers include powders commercially known as Silhap A, Silhap C, and Silhap AC from AppTec, Inc. and Apacider-AK, Apacider AW from Sangi Group in Japan. The powders are added to the hydrocolloid composition and thoroughly mixed prior to using the mixture to form the dressing devices (described below).

The hydrocolloid composition includes a hydrolloid material mixed with an adhesive material. The hydrocolloid materials that may be used include water absorbing and/or water swellable material such as carboxymethylcellulose, pectin, gelatin, high molecular weight carbowax, carboxypolymethylene, carboxymethyl starches, alginates, carrageenan, gelatine, citrus pectin, powdered pectin, synthetic or natural gums, such as gum guar, gum arabic, locust bean gum, karaya, or mixtures thereof and polyvinyl alcohol, or mixtures thereof.

The adhesive material mixed with the hydrocolloid may include any of numerous viscous, water-insoluble gum-like materials such as poly-isobutylene, silicone rubbers, polyurethane rubber, sucrose acetate isobutylate, acrylonitrile rubber, butyl rubber, natural or synthetic gum or rubber-like materials optionally in combination with plasticizers, tackifiers or solvents enhancing the adhesive characteristics or providing other enhancing characteristics of the materials or mixtures thereof. Enhancing characteristics that may be provided include a softening of the dressing layer and of the adhesiveness to permit removal of the dressing with little pain. For example, a hydrocarbon tackifier resin, mineral oil and other components may be added. Examples of hydrocarbon tackifier resins include Wingtack 95, Wingtack 10, Wingtack Plus, Wingtack Extra, Wingtack 86, Foral AX, Foral 85, Foral 105, Escorez 1000, Escorez 5300, Escorez 40105 and mixtures thereof In a preferred embodiment, the hydrocolloid adhesive composition maintains its structure, or remains intact, in the presence of moisture. In this manner, the silver ions (or other metal ions) are maintained within the dressing as the moisture from the wound exudate is absorbed. One embodiment uses carboxymethylcellulose as the preferred hydrocolloid component due to its ability to resist disintegration in the presence of moisture.

In addition, vertical absorption of the exudate by the hydrocolloid composition may be improved by the addition of a polyethylene (or, polypropolyene, polyester, or polyurethane) fiber that may be surface treated for providing an affinity promoting agent, such as a binder or adhesive material. In a preferred embodiment, a polyethlene fiber available commercially as TA-12 from Dupont is added to the hydrocolloid adhesive mixture.

Table 1 shows a formulation of one example of the dressing layer 20 of FIG. 1A in accordance with a preferred embodiment of the present invention.

TABLE 1

| Component | % by Weight |
| --- | --- |
| Elastomer - Krayton ™ | about 6% |
| Non-polar Oily Extender - Mineral Oil | about 11.5% |
| Isoprene - Natsyn Resin | about 16.0% |
| High Viscosity Adhesive Synthetic Rubber - Vistanex | about 8.0% |
| Anti-microbial agent - Bactekiller ™ | about 1.0% |
| Hydrocarbon Tackifier Resin - Foral-85 | about 13% |
| Hydrocolloid - Carboxymethylcellulose (CMC) | about 42.5% |
| polyethylene fiber - TA-12 - | about 2.0% |

The dressing layer composition shown in Table 1 advantageously provides the dressing with disinfecting capabilities without permitting silver ions to leach into the wound site. The anti-microbial agent, Bactekiller™, is a zeolite composition that permanently binds the silver ions. The dressing is also soft and conformable for maximum comfort to the patient wearing it. The tackiness of the composition maintains the dressing on the skin but the mineral oils makes the dressing soft enough to reduce the discomfort to the patient of removing the dressing. The CMC will not dissolve or disintegrate in the presence of moisture, further inhibiting the leaching of the silver ions into the wound site. The addition of TA-12 polyethylene fibers increases the vertical absorption capabilities of the dressing 10 to maximize the disinfecting action of the dressing and to keep the wound-site clean and dry.

Figure 3:
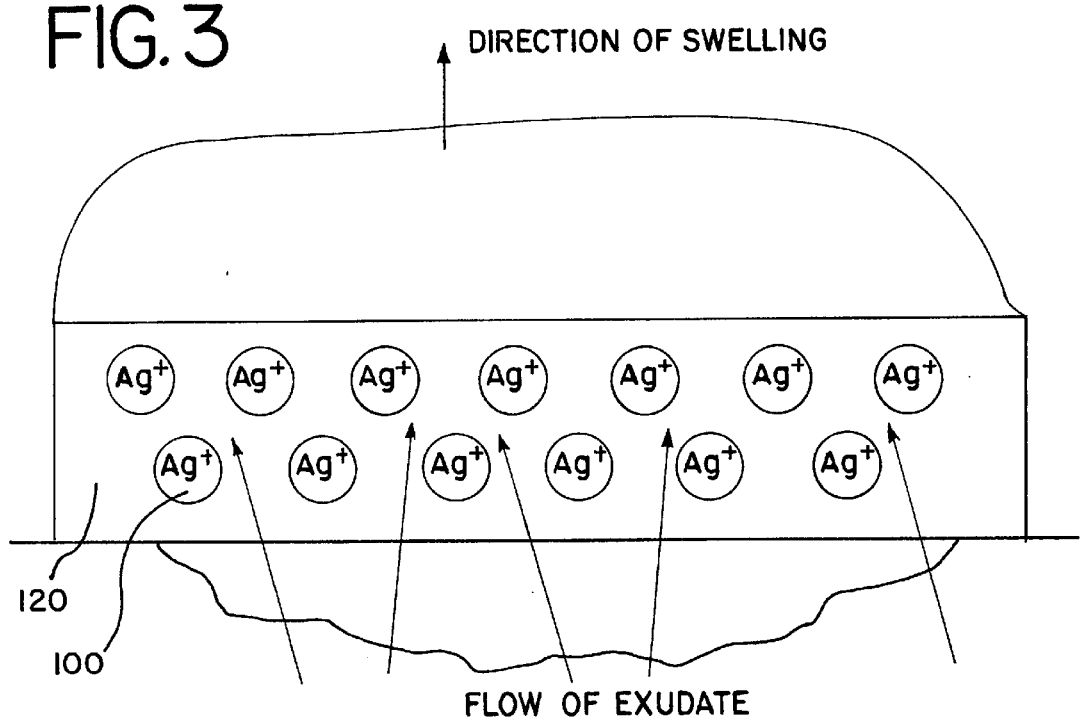
FIG. 3 is a cross-sectional view of an example of the dressing layer of FIG. 1A using a silver compound for anti-microbial affects.

FIG. 3 shows the action of the dressing layer 20 having the composition of Table 1. The moisture-absorbing properties of the CMC draws exudate from the wound at the wound site. As it is drawn in, it makes contact with the silver ions distributed throughout the dressing layer. The contact with the silver ions acts to destroy any bacteria, fungus or other microbes in the exudate and to inhibit any further growth. The moisture absorbing properties of the composition allow the dressing to continue to swell to many times its normal size. The polyethylene fibers in the composition draw the moisture vertically relative to the surface of the skin to ensure contact with the silver ions.

A dressing layer composition having the formulation of Table 1 was tested for anti-bacterial capabilities by injecting cultures of known counts of *E. Coli* and *S. Aureus*. After 10 minutes, the bacteria count was reduced by as much as 80%.

C. Method For Manufacturing Dressing

The dressing 10 of FIG. 1A may be manufactured using traditional methods of dressing manufacture. For example, Jensen, U.S. Pat. No. 5,133,821, Samuelsen U.S. Pat. No. 4,867,748 and Jensen, et al. U.S. patent application Ser. No. 09/184,811 (incorporated by reference herein) describe methods that may be used to manufacture the dressing 5.

The composition of the dressing layer 20 shown in Table 1 may be manufactured by mixing the silver compound (i.e. the Bactekiller™) with the mineral oil. The Kraton™ is heated to a temperature of about 130 degrees C. The Kraton™ is added to the mineral oil and silver compound mixture and allowed to cool to about 80 degrees C. The TA-12 and the Natsyn resin are then added to this mixture. Then, Foral-85 and the CMC are then added.

Once the dressing layer 20 composition is prepared, it may be attached to the release sheet and backing layer and shaped using, for example, the processes and methods disclosed in U.S. Pat. Ser. No. 09/184,811.

Persons of ordinary skill in the art will appreciate that variations may be made without departure from the scope and spirit of the invention. This true scope and spirit is defined by the appended claims, interpreted in light of the foregoing.

We claim:

1. A composition suitable for use as a dressing comprising:
   about 6% elastomer based on total weight of the composition;
   about 11.5% non-polar oily extender based on total weight of composition;
   about 16% isoprene based on total weight of composition;
   about 8% adhesive synthetic rubber based on total weight of a the composition;
   about 1.0% anti-microbial composition having a metallic composition, based on total weight of the composition,
   about 85.13% of hydrocarbon tackifier resin based on total weight of the composition;
   about 42.5% of calcium carboxymethylcellulose based on total weight of the composition; and
   about 2.0% polyethylene fibers coated with a water-insoluble adhesive in a network structure based on total weight of the composition.

2. The composition of claim 1 wherein the non-polar oily extender includes mineral oil.

3. The composition of claim 1 wherein the metallic composition includes a metal selected from the group consisting of silver copper, and zinc.

4. The composition of claim 1 wherein the anti-microbial agent comprises a ceramic material having the metallic composition impregnated therein.

5. The composition of claim 4 wherein the ceramic material has a matrix structure, the metallic composition comprising metallic particles trapped in the matrix structure.

6. The composition of claim 4 wherein the ceramic material is zeolite having a matrix structure, the metallic composition comprising metallic particles trapped in the matrix structure.

* * * * *